US011419697B2

United States Patent
Lebreton et al.

(10) Patent No.: US 11,419,697 B2
(45) Date of Patent: Aug. 23, 2022

(54) FOOT PEDAL FOR WIRELESS CONTROL OF A MEDICAL DEVICE

(71) Applicant: FERTON HOLDING S.A., Delémont (CH)

(72) Inventors: Etienne Lebreton, Crissier (CH); Antoine Mareschal de Charentenay, Divonne les Bains (FR)

(73) Assignee: FERTON HOLDING S.A., Delémont Schweiz (CH)

( * ) Notice: Subject to any disclaimer, the term of this patent is extended or adjusted under 35 U.S.C. 154(b) by 118 days.

(21) Appl. No.: 16/338,531

(22) PCT Filed: Sep. 11, 2017

(86) PCT No.: PCT/EP2017/072693
§ 371 (c)(1),
(2) Date: Apr. 1, 2019

(87) PCT Pub. No.: WO2018/059916
PCT Pub. Date: Apr. 5, 2018

(65) Prior Publication Data
US 2020/0038138 A1 Feb. 6, 2020

(30) Foreign Application Priority Data
Sep. 30, 2016 (DE) ...................... 10 2016 118 609.0

(51) Int. Cl.
*A61C 1/00* (2006.01)
*G05G 1/30* (2008.04)
*H01H 3/14* (2006.01)

(52) U.S. Cl.
CPC ........... *A61C 1/0023* (2013.01); *G05G 1/305* (2013.01); *H01H 3/14* (2013.01)

(58) Field of Classification Search
CPC ........ A61C 1/0023; G05G 1/305; G05G 1/30; H01H 3/14; A61B 2017/00973
(Continued)

(56) References Cited

U.S. PATENT DOCUMENTS 3,663,772 A * 5/1972 Grabel .................. G11B 15/10
200/86.5
4,114,275 A * 9/1978 Jones ................... A61C 1/0023
433/101
(Continued)

FOREIGN PATENT DOCUMENTS

DE 6603334 U 9/1969
DE 2814869 A1 10/1979
DE 202006015718 U1 1/2007

OTHER PUBLICATIONS

International Preliminary Report on Patentability for corresponding application PCT/EP2017/072693 filed Sep. 11, 2017; dated Apr. 11, 2019.
(Continued)

*Primary Examiner* — Nicholas D Lucchesi
(74) *Attorney, Agent, or Firm* — Cantor Colburn LLP

(57) ABSTRACT

A foot pedal for wireless control of a medical device, in particular a dental device, including a housing with a housing base, a cover element, which is mounted so as to be vertically displaceable relative to the housing base along an actuating direction and/or inclinable relative to the housing base, and a transmitting device arranged in the housing for wireless communication with the medical device, wherein the housing is at least partially made of a non-metallic material and the cover element is made of a metallic material, wherein in an initial state the cover element is spaced apart from the housing base and in a lowered state the cover element is offset in height with respect to the initial state in the operating direction, where the housing, in
(Continued)

particular the housing base, is configured such that, in the lowered state, a signal transmission region arranged below the cover element, viewed in the actuating direction, is provided as a communication channel for a signal emitted from the transmitting device.

9 Claims, 2 Drawing Sheets

(58) Field of Classification Search
USPC .......................................................... 433/101
See application file for complete search history.

(56) References Cited

U.S. PATENT DOCUMENTS

| | | | | |
|---|---|---|---|---|
| 4,798,535 | A * | 1/1989 | Nielsen | A61C 1/0023 433/101 |
| 5,132,498 | A * | 7/1992 | Lee | H01H 13/16 200/523 |
| 6,577,119 | B1 * | 6/2003 | Yaddehige | G01D 5/145 324/207.2 |
| 7,439,462 | B2 | 10/2008 | McCoy | |
| 7,439,463 | B2 | 10/2008 | Brenner | |
| 2007/0166661 | A1 * | 7/2007 | Brenner | A61C 1/0023 433/101 |
| 2008/0220391 | A1 * | 9/2008 | Temple | A61G 5/12 433/101 |
| 2009/0272221 | A1 * | 11/2009 | Long | G05G 1/38 74/514 |
| 2010/0230259 | A1 * | 9/2010 | Jo | G05G 1/30 200/86.5 |
| 2011/0275027 | A1 * | 11/2011 | Lint | A61C 1/0015 433/101 |
| 2012/0301844 | A1 * | 11/2012 | Guaragno | A61C 1/0023 433/101 |
| 2013/0245834 | A1 * | 9/2013 | Laxhuber | A61B 17/00 700/275 |
| 2014/0038129 | A1 | 2/2014 | Lint | |
| 2017/0119496 | A1 * | 5/2017 | Griffin | A61G 15/00 |

OTHER PUBLICATIONS

International Preliminary Report on Patentability for corresponding application PCT/EP2017/073181 filed Sep. 14, 2017; dated Apr. 11, 2019.
International Search Report for corresponding application PCT/EP2017/072693 filed Sep. 11, 2017; dated Mar. 26, 2018.
International Search Report for corresponding application PCT/EP2017/073181 filed Sep. 14, 2017; dated Jan. 15, 2018.

* cited by examiner

FOOT PEDAL FOR WIRELESS CONTROL OF A MEDICAL DEVICE

TECHNICAL FIELD

This disclosure concerns a foot pedal for wireless control of a medical device, in particular a dental device.

BACKGROUND

Such foot pedals are well known from the state of the art and are intended to provide a treating physician with a room for maneuver during treatment that allows him to continue treatment without interrupting it for manual modifications to the medical device. Instead of interrupting the treatment, he makes modifications to the medical device using the foot pedal. Essential components of the foot pedal are a housing with a housing base and a cover element that is mounted in a height-adjustable and inclinable manner along an actuating direction in relation to the housing base. Typically, the cover element rests on an actuating device arranged centrally below the cover element and being displaceable along the actuating direction, so that the cover element can be tilted to either side, in particular dumped, and can generally also be displaced additionally in the actuating direction.

Here it often proves to be useful to use a cover element made of a metal. In addition to a comparatively high mechanical and chemical load capacity, the use of a metallic cover element proves to be advantageous in that dirt on the metallic cover element can be quickly identified and easily removed. However, the use of a metallic cover element is detrimental when it is intended to be integrated into the housing having a transmitter intended for wireless communication with the medical device, as the metallic cover element shields the transmitter from signal transmission. Therefore, in the state of the art transmitting devices are usually arranged next to the metallic cover element or a plastic cover element is used. This not only negatively affects the overall visual impression of the foot pedal, but also needs more space together with the transmitting device. Also, the pedal is not so easy to disinfect and it is less stable.

BRIEF SUMMARY

It is therefore a task of the present disclosure to provide a foot pedal which, despite a metallic cover element, is compact and configured for wireless communication with the medical device.

According to the disclosure, a foot pedal for the wireless control of a medical device, in particular a dental device, is provided, comprising
  house with a housing,
  a cover element which is mounted so as to be vertically displaceable with respect to the housing base along an actuating direction and/or so as to be inclinable with respect to the housing base, and
  a transmitting device arranged in the housing for wireless communication with the medical device,
wherein the housing, in particular the housing base, is at least partially made of a non-metallic material and the cover element is made of a metallic material, wherein in an initial state the cover element is spaced apart from the housing base and in a lowered state the cover element is offset in height relative to the initial state in the actuating direction, wherein the housing, in particular the housing base, is configured in such a way that in the lowered state a signal transmission region arranged below the cover element viewed in the actuating direction, is provided as a communication channel for a signal emitted from the transmitting device.

In contrast to the state of the art, a signal transmission region is provided below the cover element, which ensures the transmission of the signal from the transmitter even when the cover element is in the lowered state. As a result, the transmitting device can be advantageously integrated into the housing, even if the cover element is made of a metallic material.

The signal transmission region is formed in particular by a gap between the cover element and a floor on which the foot pedal is arranged. By means of the housing or the housing base, the smallest possible distance for this gap can be advantageously realized in the lowered state, which still ensures signal transmission. Preferably, the cover element in the lowered state is offset in height by the maximum possible distance from the initial state. In particular, the wavelength of the outgoing signal is taken into account for the size or height of the signal transmission region in the lowered state, i.e. the gap or signal transmission range is adapted to the characteristics of the transmitter signal.

Preferably, the signal transmission region lies along the actuating direction below an outer circumference of the cover element, wherein the outer circumference limits the cover element in a sectional plane perpendicular to the actuating direction. For example, the outer circumference is configured as an edge directed towards the floor or housing floor or a collar directed towards the floor or housing floor. It is also preferred that the housing or housing base in the signal transmission region is made of non-metallic material, such as plastic. Alternatively, it is also conceivable that the bottom of the housing has a partial recess in the bottom of the housing in some areas of the signal transmission region. Furthermore, it is preferred that the transmitting device is integrated into a circuit board which is arranged inside the housing. Preferably, the cover element is completely rotationally symmetrical to a direction parallel to the actuating direction and the cover element mounted on the actuating device can be tilted or dumped to either side.

According to a further embodiment of the present disclosure, it is intended that an extension of the signal transmission region or of the gap in the lowered state in the actuating direction has a height between 1 mm and 10 mm, preferably a height between 1 mm and 6 mm and particularly preferably essentially a height of approx. 2-5 mm. In particular, this value is realized at the point with the smallest extension or extension of the signal transmission region, measured in the actuating direction. It turned out to be advantageous that such small dimensions are possible for the signal transmission region. Accordingly, the foot pedal can be embodimented to be particularly compact when viewed in the actuating direction.

Preferably it is intended that the cover element abuts the bottom of the housing when lowered. The stopping ensures advantageously that the cover element cannot be lowered any further, wherein a minimum height for the signal transmission region in the lowered state is determined. This prevents a further lowering from leading to a state in which signal transmission cannot be guaranteed in the lowered state. Preferably, a distance between the top side and the bottom side of the housing bottom, in the area of the stop, is between 2 mm and 5 mm, preferably between 2 mm and 2.5 mm, or particularly preferably substantially 2 mm. The dimensioning, preferably the thickness of the non-metallic housing base at this location determines the extension or elongation of the signal transmission region at this point, i.e. at the narrowest point.

In an advantageous embodiment of the present disclosure, it is provided that the signal transmitting device is arranged in the region of the outer periphery of the housing. Preferably the housing comprises a circumferential housing wall and the transmitting device is arranged at an area within the housing adjacent to the housing wall. This allows the transmitting device to be brought as close as possible to the signal transmission region. For example, transmitter is arranged at last third, preferably at last quarter and especially at last fifth of a distance measured from the center of housing to or the wall of housing. It turned out that such an arrangement can further improve the probability of successful signal transmission to the medical device.

The transmitting device is preferably attached directly on the bottom of the housing or is embedded in a lowered part of the housing. Due to the lowered positioning in the housing, the arrangement can be used for further optimization of the signal transmission. It is conceivable, for example, that the housing is pot-shaped and the signal transmission device is embedded in a base of the housing. Preferably, the signal transmitting device forms part of the floor. It is also conceivable that the transmitting device is arranged in the housing in such a way that in the initial state, seen in the actuating direction, it is arranged below a lower edge of the cover element or substantially at the same level as the lower edge of the cover element.

According to another embodiment of the present disclosure, it is provided that the signal emitted by the transmitting device is a WIFI signal or a Bluetooth signal. With such signals, communication ranges can be achieved that are sufficient to communicate with a medical device located in the same room with the foot pedal.

A further subject matter of the present disclosure is a foot pedal for wirelessly controlling a medical device, in particular a foot pedal in accordance with the disclosure, comprising a housing with a housing base, a cover element which is mounted so as to be vertically displaceable relative to the housing base along an actuating direction and/or so as to be inclinable relative to the housing base, the housing and the housing base being releasably connected to one another by means of a magnetic release mechanism. By means of the magnetic release mechanism, the base of the housing can be removed from the housing in a simple and uncomplicated manner without, for example, having to loose screws first. In particular, a recess open to the bottom of the housing in the assembled state is provided on an underside of the housing, which recess is intended for accommodating energy storage cells, in particular batteries. The energy storage cells serve in particular as an energy source for the transmitting device. The magnetic release mechanism proves to be particularly advantageous in order to keep the effort involved in regularly changing the energy storage cells as low as possible. A magnetic element on the housing side and a magnetic element on the bottom side of the housing are configured such that a magnetic force acting between the magnetic elements holds the magnetic parts together in the assembled state of the foot pedal.

It is preferably provided that the cover element is configured to be completely rotationally symmetrical with respect to an axis of symmetry, the axis of symmetry extending through the magnetic release mechanism or the magnetic release mechanism, viewed in a plane extending perpendicularly to the axis of symmetry, being arranged centrally in the housing. Preferably, the magnetic release mechanism is aligned flush with the actuating device when viewed in the actuating direction. Preferably, a metallic projection directed towards the cover element at the bottom of the housing forms the magnetic element on the housing side.

According to a further embodiment of the present disclosure, the foot pedal is provided with a first switch for initiating a first functionality on the medical device and a second switch for initiating a second functionality on the medical device, the first switch and the second switch being connected to the transmitting. This provides the first switch and the second switch with a common transmission device and a signal modification can be used to inform the medical device of a change of state on the foot pedal so that control via the foot pedal and the signal transmitting device is possible.

Furthermore, it is preferred that a signal amplifier for amplifying the signal from the transmitter is integrated in the bottom of the housing in the signal transmission region. For example, the signal amplifier is a repeater that ensures that the signal, especially the radio signal, is amplified in the area of the transmission range at the bottom of the housing in such a way that a signal size as large as possible can be provided to the medical device or a corresponding range can be achieved with the signal.

BRIEF DESCRIPTION OF THE DRAWINGS

Further advantages and characteristics result from the following description of preferred embodiments of the subject matter of the disclosure with reference to the attached figures. Individual characteristics of the individual embodiment can be combined with each other within the disclosure Show it.

DETAILED DESCRIPTION

Figure 1:
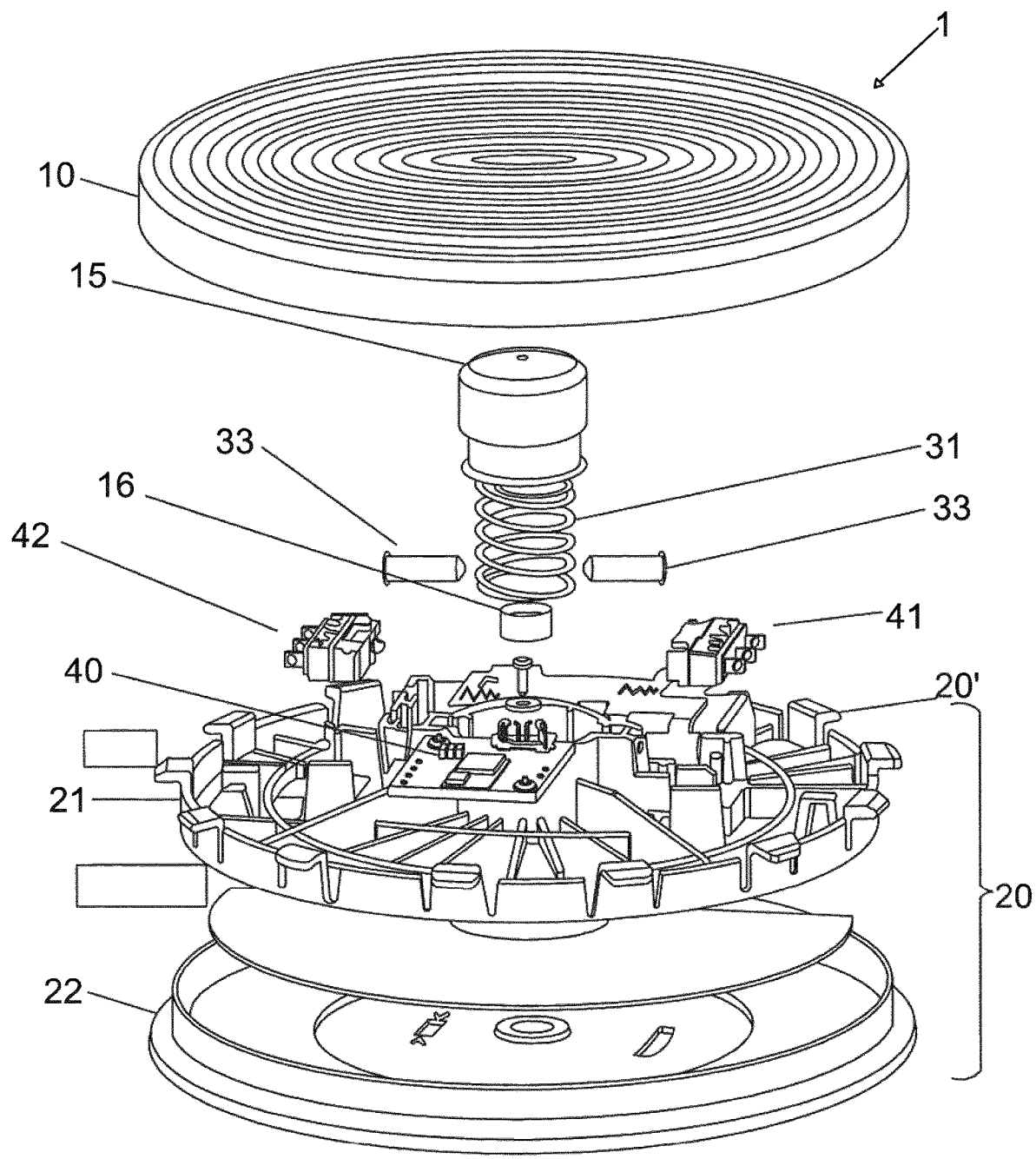
FIG. 1 schematic exploded view of a foot pedal according to a preferred embodiment of the present disclosure, and FIGS. 2a to 2d sectional views of the foot pedal from FIG. 1 in different operating conditions.

FIG. 1 shows a schematic exploded view of a foot pedal 1 according to a preferred embodiment of the present disclosure. In particular, the foot pedal 1 is one intended to control a medical device (not shown), preferably a dental device. The foot pedal 1 should be used to make settings on the medical device so that the user does not have to interrupt his work, for example a treatment measure on the patient, in order to operate the medical device manually.

In addition to a housing 20 with a housing base 22, an essential component of the embodiment example shown in FIG. 1 is also a cover element 10, which is height-adjustable in relation to the housing base 22 along an actuating direction B and in this case is also inclinably mounted. Specifically, the cover element 10 rests centrally on an actuating device 15. By centrally resting on the actuating device 15, the cover element 10 can be tilted or inclined towards all sides and by the contact between the cover element 10 and the actuating device 15, the actuating device 15 is displaced in actuating direction B when a force, in particular a force caused by a foot, is applied to the cover element 10 in the vertical direction. A height offset of the actuating device can occur both when stepping on the edge area and when stepping on the central area. The height offset of the actuating device, when stepping on the edge area, is supported by the fact that during tilting the movement of the cover element on the side opposite to the actuated edge area is limited upwards, i.e. in a direction opposite to the actuating direction. In order to return the actuating device 15 to its initial state, a spring 31 is provided, which is connected on one side to the housing base 22 or a housing base 20' (FIG. 2) and on the other side to the actuating device 15.

Depending on the position and magnitude of the force applied, different height offsets are caused by the foot stepping on the cover element 10. If, for example, a force acts on the edge area of the cover element 10, the cover element 10 is tilted around a lever point provided by the actuating device 15 or a lever surface provided by the actuating device. In addition to the inclination, a height offset of the height-adjustable mounted actuating device 15 is also initiated. However, this height offset is smaller than that caused by a force of the same magnitude when the force acts above the actuator device 15 and parallel to the actuating direction 15 on the cover element 10, i.e. substantially vertically in this example. Accordingly, the different height offsets can be used to differentiate between two types of foot pedal 1 actuation, whereby different functionalities can be assigned to the different types of actuation. In particular, a first functionality can be assigned to an stepping on the edge area and the resulting tilting of the cover element 10, and a second functionality can be assigned to stepping on the central area of the cover element 10.

In order to take advantage of this difference in height offset in the different actuations to differentiate the actuations with the foot, in particular a first switch 41 and a second switch 42 are provided, which are arranged vertically offset from one another, wherein the first switch 41 can be actuated within a first height offset section when the actuating device 15 moves in the actuating direction B and the second switch 42 can be actuated within a second height offset section. The second height offset section in actuating direction B is directly connected to the first height offset section. The first switch 41 and the second switch 42 are actuated, for example, by pins 33 which can be displaced perpendicularly to the actuating direction B and which are pretensioned against an outside of the actuating device 15 by means of spring elements (not shown). The outside of the actuating device 15 has an outer contour, for example in the form of a projection or ramp. When the actuating device 15 moves in actuating direction B, this outer contour interacts with the sliding pins 33 in such a way that the pins 33 are pushed radially outwards away from the side, i.e. along a direction perpendicular to the actuating direction B and against the restoring force of the spring elements, whereby the first switch 41 or second switch 42 can be actuated. By the fact that the first switch 41 and the second switch 42 are arranged vertically offset from each other, the first switch 42 and the second switch 42 can be switched successively by a movement of the actuating device 15 in the actuating direction B, in particular depending on the respective height offset of the actuating device 15, independent of the position of the force acting on the edge area of the cover element, in particular the circular cover element.

For wireless communication with the medical device, a transmitting device 40 is provided which is arranged inside the housing 20 and which is connected to the first switch 41 and the second switch 42. Preferably, the transmitting device 40 transmits a WIFI signal or a Bluetooth signal to communicate with the medical device. The transmitting device is supplied by an energy storage cell 45, e.g. a battery, located inside the housing 20. Furthermore, it is intended that the cover element 10 is made of a metallic material so that signal transmission via the cover element 10 is excluded. In other words: the cover element 10 shields the transmitter 40. The signal is transmitted accordingly via a signal transmission region 44, which is limited on one side by the cover element 10 and on the other side by a floor on which the foot pedal 1 is arranged.

Figure 2A:
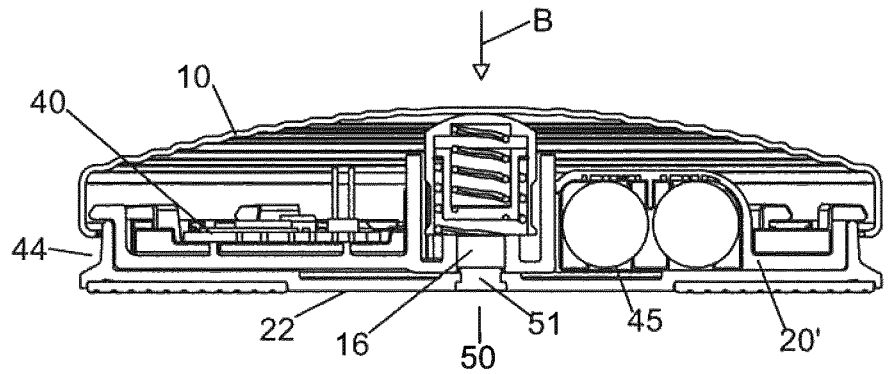

In FIGS. 2a to 2d the foot pedal 1 from FIG. 1 is shown in different operating states. FIG. 2a shows the cover element 10 in its initial state. In this initial state, no external force acts on the cover element 10 and the spring 31 distances the cover element 10 from the housing floor 22. Seen in operating direction B, a sufficiently large gap is thus formed below the cover element 10, specifically between the cover element 10 and a floor on which the foot pedal 1 is arranged, which serves as the signal transmission area 44.

Figure 2B:
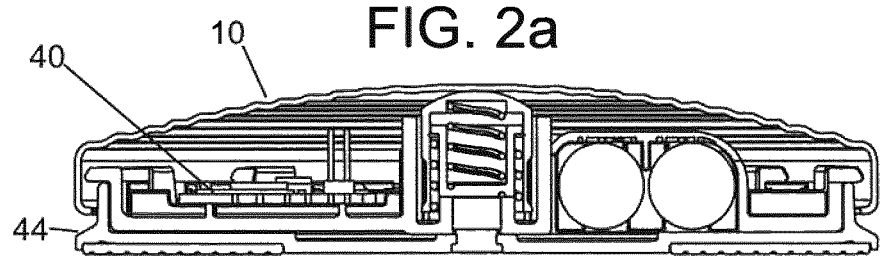
Figure 2C:
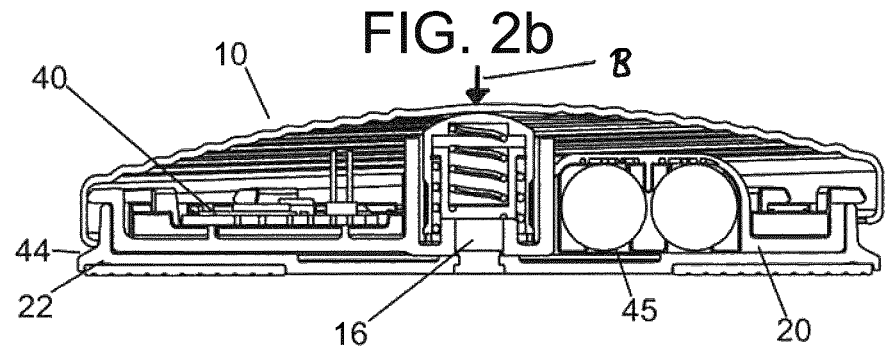
Figure 2D:
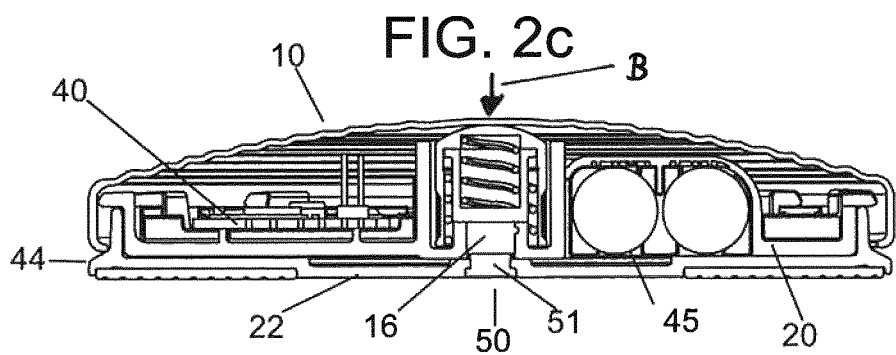

In FIGS. 2b and 2c, the cover element 10 is shown inclined or tilted, whereas in FIG. 2c, the cover element 10 at least partially abuts with the housing bottom 22. In any case, a gap of sufficient size for signal transmission is formed on the side opposite an area in which the cover element 10 abuts the housing base 22 in the direction perpendicular to the actuating direction. FIG. 2d shows the cover element 10 in a lowered state, in which the cover element 10 with its collar at its outer circumference lies against the housing base 22. Here it is provided that the housing base 22 is configured in such a way that a signal transmission region 44 is also provided in the lowered state.

In the embodiment shown in FIGS. 2a to 2d, the housing base 22 is configured in such a way that the lowered cover element 10 abuts against an upper side of the housing base 22, in particular against a circumferential shoulder on the housing base 22. The distance between the top side and a bottom side of the housing base 22 opposite the top side in the actuating direction is dimensioned in such a way that the housing base 22 provides a signal transmission region 44 in the lowered state. For this purpose, the housing base 22 is in particular recessed in a region located between the transmitting device and an outer circumference of the housing base and/or made of a non-metallic material in order to ensure signal continuation. Preferably, a distance between the top side and the bottom side of the housing bottom 22 between 2 mm and 5 mm, preferably between 2 mm and 2.5 mm, or particularly preferably substantially 2 mm is required.

It is also provided that the housing 20 or a housing base body 20' has a circumferential housing wall 21 (FIG. 1), the transmitting device 40 being arranged in a region adjacent to the housing wall 21 within the housing 20. In order to further support the signal transmission through the housing base 22, the transmitting device is arranged in a lowered area of the housing 20 or the housing base 20'.

Furthermore, it is preferably provided that the housing 20 is configured as an insert in the form of a basic housing body 20' which is connected to the housing base 22. Preferably, the case bottom 22 is bound to the case 20 via a magnetic release mechanism 50. For this purpose, the housing base 22 comprises a magnet 51 which interacts with a magnetic part of the housing 20 or the housing base 20'. Preferably the magnetic release mechanism 50 is located below the actuating device 15. In particular, a projection 16, against which the actuator 15 comes into abutment during movement along the actuating direction B, forms the magnetic part of the housing 20, which retains the housing base 22 with its magnets 51 in the assembled state.

The magnetic release mechanism 50 allows an uncomplicated release of the case bottom 22 from the case 20. Furthermore, the magnetic release mechanism 50, if it is centrally mounted on the case bottom 22, as shown in the figures, allows a rotational movement of the case base 20' and the cover element 10 connected to it around the case bottom 22, which is usually adherently connected to the floor. For this purpose, the opposing surfaces of the magnet 51 and the magnetic part of the housing 20, such as the projection 16, are mounted in such a way that a rotating movement is made possible. Smooth surfaces that slide on top of each other are preferred.

Preferably, the housing on its side facing the housing base 22 is configured in such a way that a compartment for energy storage cells 45 is freely accessible when the housing base 22 is separated from the housing 20. Together with the magnetic release mechanism 50, it is possible to simplify the change of the energy storage cells 45, which is regularly required for the supply of the transmitting device 40 in the housing.

The invention claimed is:

1. A Foot pedal for wireless control of a medical device, in particular a dental device, comprising
a housing with a housing base,
a cover element, which is mounted so as to be one or more of vertically displaceable relative to the housing base along an actuating direction and inclinable relative to the housing base, and
a transmitting device arranged in the housing for wireless communication with the medical device,
wherein the housing is at least partially made of a non-metallic material and the cover element is made of a metallic material,
wherein in an initial state the cover element is spaced apart from the housing base and in a lowered state the cover element is offset in height with respect to the initial state in the actuating direction, and
wherein the housing is configured such that, in the lowered state, a signal transmission region arranged below the cover element, viewed in the actuating direction, is provided as a communication channel for a signal emitted from the transmitting device, wherein the transmitting device is arranged in a region of the outer periphery of the housing, wherein the signal transmitting device is arranged in a last third of a distance measured from the center of the housing to the wall of the housing.

2. The foot pedal according to claim 1, wherein an extension of the signal transmission region in the lowered state, viewed in the actuating direction, has a height between 1 mm and 10 mm.

3. The foot pedal according to claim 1, wherein the cover element comes in abutment with the housing base in the lowered state.

4. The foot pedal according to claim 1, wherein the transmitting device is attached directly on a bottom of the housing or is embedded in a lowered portion of the housing.

5. The foot pedal according to claim 1, wherein the signal transmitted by the transmitting device is a WIFI signal or a Bluetooth signal.

6. A foot pedal for wireless control of a medical device, comprising
a housing with a housing base,
a cover element which is mounted so as to be one or more of vertically displaceable relative to the housing base along an actuating direction and so as to be inclinable relative to the housing base,
wherein the housing and the housing base are detachably connected to one another by means of a magnetic release mechanism.

7. The foot pedal according to claim 6, wherein the cover element is configured to be completely rotationally symmetrical with respect to an axis of symmetry, and wherein the axis of symmetry runs through the magnetic release mechanism, or the magnet release mechanism is arranged centrally in the housing as seen in a section plane running perpendicularly to the axis of symmetry.

8. The foot pedal according to claim 6, wherein the foot pedal has a first switch for initiating a first functionality on the medical device and a second switch for initiating a second functionality of the medical device, wherein the first switch and the second switch are connected to a transmitting device.

9. The foot pedal according to claim 8, wherein a signal amplifier for amplifying a signal from the transmitting device is integrated in the housing base in a signal transmission region.

* * * * *